United States Patent [19]

Ogino et al.

[11] 4,424,037
[45] Jan. 3, 1984

[54] DENTAL IMPLANT

[75] Inventors: Makoto Ogino, Yokohama; Takamitsu Fujiu, Tokyo; Toshihiko Futami, Kawasaki; Michio Kariya, Yokohama; Takeo Ichimura, Tokyo, all of Japan

[73] Assignee: Nippon Kogaku K.K., Tokyo, Japan

[21] Appl. No.: 343,833

[22] Filed: Jan. 29, 1982

[30] Foreign Application Priority Data

Feb. 4, 1981 [JP] Japan .................................. 56-14636

[51] Int. Cl.³ .............................................. A61C 8/00
[52] U.S. Cl. .................................... 433/173; 433/201
[58] Field of Search ............... 433/173, 174, 175, 176, 433/201; 3/1.9, 1.91, 1.911, 1.912, 1.913; 128/92 C

[56] References Cited

U.S. PATENT DOCUMENTS

| 3,981,736 | 7/1976 | Broemer et al. ................... 106/39.6 |
| 4,120,730 | 10/1978 | Trojer et al. ....................... 106/39.6 |
| 4,164,794 | 8/1979 | Spector et al. ...................... 433/201 |
| 4,171,544 | 10/1979 | Hench et al. ........................ 433/173 |
| 4,234,972 | 6/1980 | Hench et al. ............................ 3/1.9 |

FOREIGN PATENT DOCUMENTS

| 2708917 | 9/1978 | Fed. Rep. of Germany ........... 3/1.9 |
| 1446097 | 8/1976 | United Kingdom ................... 3/1.91 |

*Primary Examiner*—John J. Wilson
*Attorney, Agent, or Firm*—Wegner & Bretscheider

[57] ABSTRACT

Dental implant is composed of a core and a coating layer of a biologically active glass or glass-ceramic material covering at least a part of the core to be embedded in the jawbone. The glass or glass-ceramic layer comprises at least two separated portions spaced from each other.

2 Claims, 13 Drawing Figures

DENTAL IMPLANT

BACKGROUND OF THE INVENTION

1. Field of the Invention

The present invention relates to a dental implant.

2. Description of the Prior Art

In order to replace lost natural teeth there have been proposed various dental implants, among which proposed recently are dental implants utilizing biologically active materials such as disclosed in the U.S. Pat. Nos. 3,981,736, 4,120,730 and 4,234,972. The biologically active material means a material capable of forming a direct chemical bond with a hard tissue, particularly a bone, in the organism, and such dental implant therefore provides a strong artificial tooth directly bonded with the jawbone. A representative example of such implant is composed of a core member of an elevated mechanical strength such as of a metal, coated with said biologically active material at least in a part to be embedded in the jawbone. For said biologically active material presently employed are biologically active glasses or glass-ceramics. However such materials tend to cause cracks under an abnormally strong local force, and such cracks gradually propagate in time to cause destruction of the entire coating material or peeling of the coating material from the core member.

SUMMARY OF THE INVENTION

The object of the present invention is to provide a dental implant composed of a core member covered with a biologically active glass or glass-ceramic material, in which a partial destruction in the glass or glass-ceramic coating does not propagate to the entire coating layer.

The above-mentioned object can be achieved according to the present invention by a dental implant composed of a core member of an elevated mechanical strength coated with a biologically active glass or glass-ceramic material at least in a part to be embedded in the jawbone, wherein said coating layer comprises at least two separate portions spaced from each other.

Now the dental implant of the present invention will be explained in detail in the following.

The core member can be, for example, of an essentially inverted conical form composed, as shown in a perspective view in FIG. 1A, of a root portion $1a$ to be embedded in the jawbone and a support portion $1b$ for mounting an upper structure such as an artificial crown, or of an essentially inverted conical form composed, as shown in a perspective view in FIG. 2A, of a root portion $1a$ having a recess $1b$ for supporting the upper structure, or of an essentially rectangular structure provided, as shown in a perspective view in FIG. 3A, with two root portions $1a$, $1a'$ and a recess $1b$ for supporting the upper structure. Such core member structures are partly already known.

FIGS. 1B, 2B and 3B show, in cross-sectional views, the state of a jawbone with a dental implant composed of the above-mentioned core member coated with a biologically active glass or glass-ceramic material entirely or at least in a part of said core member to be embedded in the jawbone, wherein shown are the core member 1, the root portion $1a$ implanted in the jawbone, the support portion or recess $1b$ for supporting the upper structure, the glass or glass-ceramic material 2, a post core 3 for connecting said implant with the upper structure such as an artificial crown, an artificial crown 4, the jawbone 5, and gingiva 6. In these drawings it is to be noted, however, that the coating layer 2 of said biologically active glass or glass-ceramic material is not illustrated in the divided structure explained in the foregoing.

The material itself of the core member 1 is known and can be composed of a metal having an elevated mechanical strength and an adaptability to the organism, such as Co-Cr alloys, Ni-Cr alloys, stainless steels, titanium, titanium alloys, platinum, platinum-rhodium alloys or alumina.

Also the biologically active glass or glass-ceramic material itself is already known and can be composed for example of glass compositions disclosed in the U.S. Pat. Nos. 4,234,972, 3,981,736 and 4,210,730. Another preferred example is the biologically active glass or glass-ceramic material having the following basic composition.

| | |
|---|---|
| $SiO_2$ | 35–60 mol. % |
| $B_2O_3$ | 5–15 mol. % |
| $Na_2O$ | 10–30 mol. % |
| CaO | 5–40 mol. % |
| $TiO_2$ | 0.5–10 mol. % |
| $P_2O_5$ | 0–15 mol. % |
| $K_2O$ | 0–20 mol. % |
| $Li_2O$ | 0–10 mol. % |
| MgO | 0–5 mol. % |
| $Al_2O_3 + ZrO_2 + Nb_2O_3$ | 0–8 mol. % |
| $La_2O_3 + Ta_2O_5 + Y_2O_3$ | 0–15 mol. % |
| $F_2$ | 0–15 mol. % | which was filed by some of the present inventors as the U.S. patent application Ser. No. 270,588 on June 4, 1981.

Said biologically active glass or glass-ceramic material covers said core member in the entire surface thereof or at least a part thereof to be embedded in the jawbone, preferably with a thickness in a range from 0.1 to 2 mm.

The improvement achieved by the present invention is characterized by a fact that the coating layer of said biologically active glass or glass-ceramic material is divided into mutually separate at least two portions. The separating zone for separating the partial coating layers with a distance therebetween can be composed of a mere gap, a rib protruding from the core member, or another elastic or tenacious material adaptable to the organism. The width of such separating zone can be in a range from ca. 0.2 to 1 mm.

DESCRIPTION OF THE PREFERRED EMBODIMENTS

Now the present invention will be clarified in further detail by the following non-limitative embodiments.

EXAMPLE 1

Figure 1A:
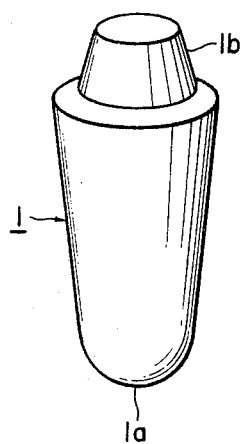
FIGS. 1A, 2A and 3A are perspective views showing different embodiments of the core member.
Figure 1B:
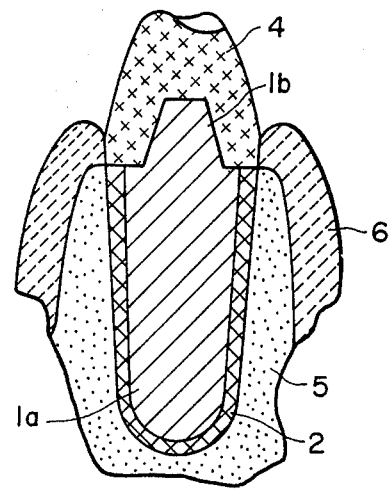
FIGS. 1B, 2B and 3B are cross-sectional views showing different examples of conventional dental implant composed of a core member coated with a biologically active glass or glass-ceramic material, placed in the jawbone.
Figure 2A:
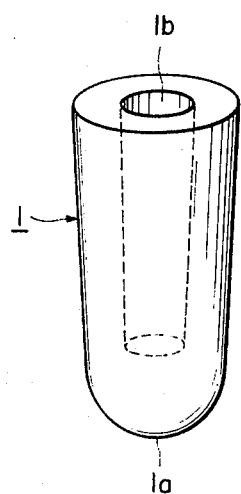
Figure 2B:
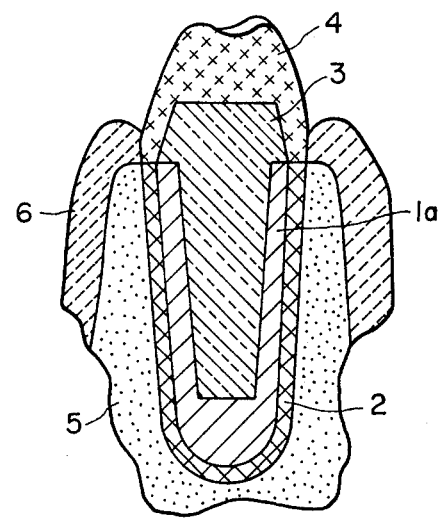
Figure 3A:
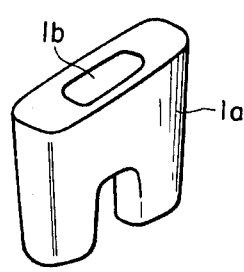
Figure 3B:
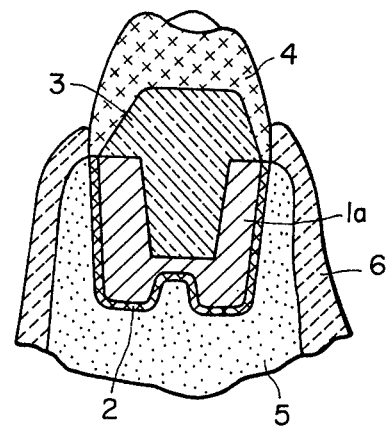
Figure 3C:
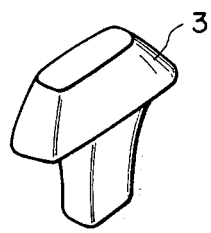
FIG. 3C is a perspective view of a post core for connecting the dental implant with an artificial crown.
Figure 4A:
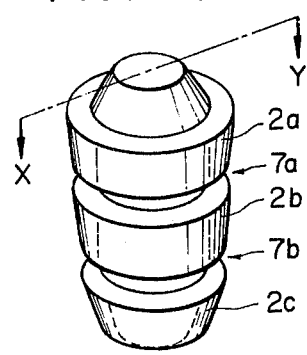
FIG. 4A is a perspective view of a dental implant embodying the present invention.
Figure 4B:
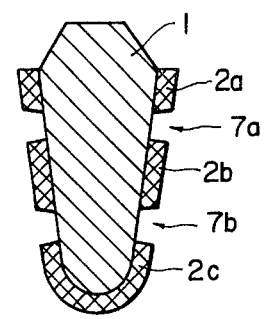
FIG. 4B is a cross-sectional view of the dental implant shown in FIG. 4A along a line X-Y therein.

As shown in FIGS. 4A and 4B, an essentially inverted conical core member 1 having a maximum diameter of 4 mm and a height of 12 mm is coated with a biologically active glass or glass-ceramic material 2 with a thickness of 0.5 mm.

Said coating layer is divided into three zones 2a, 2b and 2c by two separating zones 7a, 7b each composed of an annular groove of a width of 2 mm.

The presence of such separating zones 7a, 7b prevents the eventual breakage in a part of said coating layer from propagating to other parts of the coating layer. Consequently the coating layer should preferably divided into as many zones as possible, though such division will involve complication preparation.

In the present embodiment said separating zones are constituted by grooves, allowing intrusion of the bone newly formed by the proliferating effect of the biologically active material, thereby generating a mechanical bonding, in addition to the chemical bond, between the dental implant and the jawbone and enabling firm fixation of said implant in the jawbone. Also such bone intrusion can be accelerated by filling said grooves with a biodegradable material which stimulates the growth of new bone and is replaced by such bone.

Figure 5:
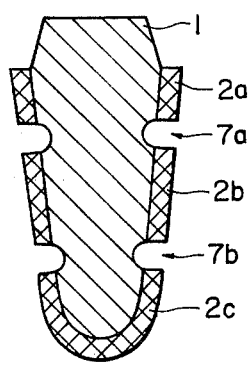
FIGS. 5 and 6 are cross-sectional views showing other embodiments of the present invention.

FIG. 5 shows a variation of the above-mentioned dental implant, in which said grooves 7a, 7b are formed deeper to reach a part of the core member 1.

EXAMPLE 2

Figure 6:
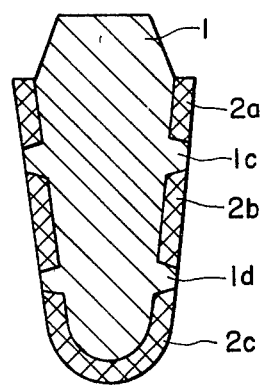

As shown in FIG. 6, the core member 1 in this embodiment is of an essentially inverted conical shape with a maximum diameter of 5 mm and a height of 17 mm and is provided, on the lateral face thereof, with annular ribs 1c, 1d of 1 mm in width and 0.8 mm in height.

The coating layer of the biologically active glass or glass-ceramic material, having a thickness of 0.8 mm, is divided into three zones 2a, 2b and 2c by said ribs 1c, 1d, which constitute the separating zones of the present invention.

EXAMPLE 3

Figure 7:
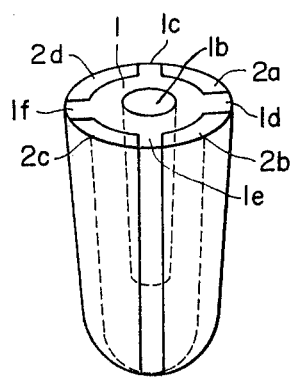
FIGS. 7 and 8 are perspective views showing still other embodiments of the present invention.

As shown in FIG. 7, the core member 1 in this embodiment is of a bullet form having a diameter of 4 mm and a height of 7 mm and further having a recess 1b of a diameter of 2 mm and a depth of 5 mm. Said core member 1 is further provided with vertical ribs 1c, 1d, 1e and 1f each 0.5 mm wide and tall.

The coating layer of the biologically active glass layer, having a thickness of 0.5 mm, is divided into four zones 2a, 2b, 2c and 2d by said ribs 1c, 1d, 1e and 1f.

EXAMPLE 4

Figure 8:
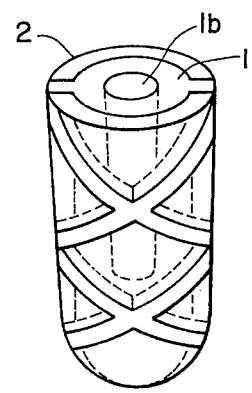

As shown in FIG. 8, the dental implant of this embodiment is composed of a bullet-shaped core member 1 of a diameter of 6 mm and a height of 9 mm having a recess 1b of a diameter of 2 mm and a depth of 5 mm, and a coating layer 2 of the biologically active glass having a thickness of 0.8 mm.

Said core member 1 is provided with grating-formed ribs each having 0.8 mm in width and in height, which divide the coating layer 2 into plural areas, thus functioning as the separating zones of the present invention.

As explained in the foregoing, the present invention allows to prevent an eventual breakage in a part of the coating layer of the biologically active glass or glass-ceramic material on the dental implant from propagating to other parts of said coating layer, thereby ensuring firm fixation of the dental implant to the jawbone by the undamaged coating layer.

We claim:

1. In a dental implant comprising a core member and a coating layer of a biologically active glass or glass-ceramic material covering at least part of the portion of said core member which is to be embedded in the jawbone, the improvement wherein said coating layer comprises at least two portions completely separated from each other, thereby preventing propagation of cracks over the entire coating layer.

2. A dental implant according to the claim 1, wherein a rib protruding from said core member is present between said separated zones of the coating layer.

* * * * *